United States Patent [19]

Gruber

[11] Patent Number: 5,468,873
[45] Date of Patent: Nov. 21, 1995

[54] PROCESS FOR PREPARING AMIDE N-CARBOX-AMIDES

[75] Inventor: John M. Gruber, Mountain View, Calif.

[73] Assignee: Catalytica, Inc., Mountain View, Calif.

[21] Appl. No.: 424,774

[22] Filed: Apr. 18, 1995

Related U.S. Application Data

[62] Division of Ser. No. 188,432, Jan. 28, 1994.

[51] Int. Cl.$^6$ ................................................. C07D 209/30
[52] U.S. Cl. ........................... 548/486; 548/431; 548/450; 564/45; 564/46
[58] Field of Search ...................... 548/486, 431, 548/450; 564/45, 46

[56] References Cited

PUBLICATIONS

CA114–184822w Preparation of N-(α–alkoxyethyl)carboxamides. Sugita et al., p. 724, 1991.

*Primary Examiner*—Joseph K. McKane
*Attorney, Agent, or Firm*—John H. Grate

[57] ABSTRACT

The present invention provides a process for preparing 2-oxindole-1-carboxamides, comprising reacting N-acyl 2-oxindole-1-carboxamides with alcohols in the presence of aprotic weak Lewis acid catalysts. In certain processes of the present invention a 2-oxindole-1-carboxamide is prepared from a 2-oxindole by reacting the 2-oxindole with an acyl isocyanate to produce the N-acyl 2-oxindole-1-carboxamide as an intermediate, which is then reacted with alcohol in the presence of aprotic weak Lewis acid catalysts The N-acyl 2-oxindole-1-carboxamide intermediate may be converted to the 2-oxindole-1-carboxamide without isolation.

11 Claims, No Drawings

PROCESS FOR PREPARING AMIDE N-CARBOX-AMIDES

This application is a division of application Ser. No. 08/188,432, filed Jan. 28, 1994, now allowed.

FIELD OF THE INVENTION

This invention relates generally to preparing 2-oxindole-1-carboxamides. More specifically, it relates to preparing 2-oxindole-1-carboxamides by alcoholysis of N-acyl 2-oxindole-1-carboxamides. It further relates to preparing 2-oxindole-1-carboxamides by reacting a 2-oxindole with an acyl isocyanate to produce an N-acyl 2-oxindole-1-carboxamide which is then alcoholyzed to a 2-oxindole-1-carboxamide. 2-oxindole-1-carboxamides are valuable analgesic and anti-inflammatory agents and/or are useful as intermediates for such agents.

BACKGROUND OF THE INVENTION

Graf, Angew, *Chem. Internat.*, Edit 7:172–182 (1968) describes addition of amines and carboxamides to chlorosulfonyl isocyanate to produce N-chlorosulfonylureas and acyl N-chlorosulfonylureas, respectively.

U.S. Pat. Nos. 3,634,453, 4,556,672 and 4,569,942, issued Jan. 11, 1972, Dec. 3, 1985 and Feb. 11, 1986, respectively, describe preparation of 2-oxindoles of formula (I) below.

U.S. Pat. Nos. 4,652,658 and 4,665,194, issued Mar. 24, 1987 and May 12, 1987, respectively, describe a process for making 2-oxindole-1-carboxamides by reacting a 2-oxindole with chlorosulfonyl isocyanate to produce a N-chlorosulfonyl-2-oxindole-1-carboxamide which is then hydrolyzed to a 2-oxindole-1-carboxamide.

U.S. Pat. Nos. 4,952,703 and 5,086,186, issued Aug. 28, 1990 and Feb. 2, 1992, respectively, and incorporated by reference entirely, describe a process for making 2-oxindole-1-carboxamides by reaction of 2-oxindoles with trichloroacetyl isocyanate to produce N-trichloroacetyl-2-oxindole-1-carboxamides which are then hydrolyzed to 2-oxindole-1-carboxamides. The so-called hydrolysis of the N-trichloroacetyl-2-oxindole-1carboxamides, is said to be accomplished under acid conditions by treating with an acidic reagent, such as a mineral acid (surfuric, hydrochloric), camphorsulfonic acid, or toluenesulfonic acid, in the presence of water or an alcohol with or without an additional solvent. Favored solvents are said to be alcohol (C1–4) solvents. The preferred acidic agent is said to be surfuric acid in methanol. Only protic acidic reagents are specifically disclosed; only surfuric acid is demonstrated by the working examples.

U.S. Pat. Nos. 4,952,703 and 5,086,186 further state that the disclosed process is adaptable to a one-pot process, without isolation of the intermediate N-trichloroacetyl-2-oxindole-1-carboxamide. They still further declare that the trichloroacetyl isocyanate can be used in premade form or it can be prepared in situ by reacting trichloroacetyl chloride and potassium cyanate in a reaction-inert solvent such as acetone. They specifically state, "The in situ preparation comprises reacting trichloroacetyl chloride and potassium cyanate in a reaction-inert solvent such as acetone in a molar ratio of from about 1:1 to 1:5. In practice, it is preferred to first react the trichloroacetyl chloride and potassium cyanate in acetone at about room temperature and then to add the oxindole reactant in acetone solution. The reaction is gradually heated to about 50° C. up to the reflux temperature of the solvent until substantially complete as indicated by thin layer chromatography (TLC). The trichloroacetyloxindole carboxamide product can be recovered by known procedures. Alternatively, the trichloroacetyloxindole carboxamide is hydrolyzed in the same reaction vessel by addition of an acidic reagent, preferably surfuric acid/methanol as described above." Neither the suggested one-pot process (without the recovery of N-trichloroacetyl-2-oxindole-1-carboxamide intermediate), nor the prescribed preparation of trichloroacetyl isocyanate in situ is demonstrated by the working examples.

While investigating the potential for practical use of the process described in the aforementioned U.S. Pat. Nos. 4,952,703 and 5,086,186, the present inventor discovered that the prescribed one-pot adaptation with in situ preparation of the trichloroacetyl isocyanate gives poor yields of 2-oxindole-1-carboxamide in the so-called hydrolysis step (which is actually an alcoholysis) compared to the step-wise process with isolation of the N-trichloroacetyl-2-oxindole-1-carboxamide intermediate or to the one-pot process using premade trichloroacetyl isocyanate. This result is believed to be due to the presence of acetone, the prescribed solvent for the in situ preparation of the trichloroacetyl isocyanate, when carried forward, as prescribed, into the alcoholysis step. Acetone is known to undergo various self-condensation and cross condensation reactions in the presence of acidic reagents.

The present inventor further discovered that the protic add reagent used in the alcoholysis step gives less-than-desired selectivity towards alcoholysis at the intended terminal amide bond. The N-trichloroacetyl-2-oxindole-1-carboxamide intermediates have four amide bonds (carbonyl carbon-nitrogen bonds) which may be susceptible to alcoholysis, as indicated by the crooked "break" lines in the formula (IV). To the extent that alcoholysis occurs at the unintended amide bonds in either the N-trichloroacetyl-2-oxindole-1-carboxamide reactant or the desired 2-oxindole-1-carboxamide product, the product yield is decreased. For at least certain desired 2-oxindole-1-carboxamide products, for example 5-chloro-2-oxindole-1-carboxamide (X=5-Cl, Y=H, R=H), the protic acid reagent causes significant methanolysis of the cyclic amide bond in the oxindole structure leading to the ring-opened by-product of formula (V) which is difficult to remove from the desired product. This results in not only a decreased yield but product of lesser purity, unless additional purification measures are undertaken which may in turn result in a still lower recovered yield.

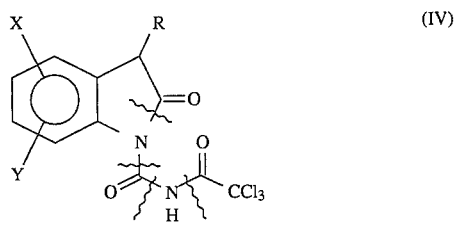

(IV)

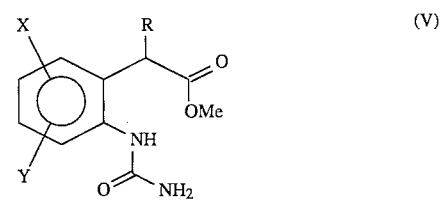

(V)

SUMMARY OF INVENTION

The present invention provides an improved process, having practical utility, for preparing 2-oxindole-1-carboxamides in yields and purity at least as good as those obtainable by known methods, comprising reacting N-acyl 2-oxindole-1-carboxamides with alcohols in the presence of aprotic weak Lewis acid catalysts. The weak Lewis acid catalysts of the present invention provide improved reaction rates and selectivities in the alcoholysis of N-acyl 2-oxindole-1-carboxamides and decrease the formation of by-products that are difficult to remove from the 2-oxindole-1-carboxamide product.

In certain processes of the present invention, a 2-oxindole-1-carboxamide is produced from a 2-oxindole by reacting the 2-oxindole with an acyl isocyanate to produce the N-acyl 2-oxindole-1-carboxamide as an intermediate, which is then alcoholyzed to a 2-oxindole-1-carboxamide in the presence of a weak Lewis add catalyst. The N-acyl 2-oxindole-1-carboxamide intermediate may be converted to the 2-oxindole-1-carboxamide without isolation.

In certain other processes of the present invention, an acyl isocyanate is produced in solution by reacting an acyl chloride with a cyanate salt and is reacted, without isolation, with a 2-oxindole to produce the N-acyl 2-oxindole-1-carboxamide as an intermediate, which is then alcoholyzed to a 2-oxindole-1-carboxamide in the presence of a weak Lewis add catalyst. The present invention provides solvent systems and solvent manipulations that provide an efficient process having no intermediate isolations.

Compounds of formula (III) below wherein R is hydrogen are useful as intermediates for preparation of analgesic and anti-inflammatory compounds wherein R is —C(O)R¹ wherein R¹ is as defined below.

More generally, the present invention provides a process for preparing amide N-carboxamides, comprising reacting N'-acyl amide N-carboxamides with alcohols in the presence of aprotic weak Lewis acid catalysts. It further provides a process for preparing an amide N-carboxamide from an primary or secondary amide, comprising reacting the amide with an acyl isocyanate to produce an N'-acyl amide N-carboxamide as an intermediate, which is then reacted with an alcohol in the presence of a weak Lewis acid catalyst to produce the amide N-carboxamide. The N'-acyl amide N-carboxamide intermediate may be converted to the amide N-carboxamide without isolation.

The amide N-carboxamide is also known as an N-acylurea. When prepared from the corresponding amide, the N-acyl moiety in the N-acylurea is the same as in the amide starting material. The N'-acyl amide N-carboxamide is also known as an N,N'-diacylurea. When prepared from the amide and an acyl isocyanate, the N-acyl moiety in the N,N'-diacylurea is the same as in the amide starting material and the N'-acyl moiety is the same as in the acyl isocyanate reactant. By selecting an N'-acyl moiety, as described below, that is more electron withdrawing than the N-acyl, the desired amide N-carboxamide can be obtained in good selectivity from the alcoholysis of the N,N'-diacylurea in the presence of the weak Lewis add catalysts of the present invention.

Certain secondary amides suitable for conversion to amide N-carboxamides by the inventive process are cyclic amides, also known as lactams. 2-oxindoles are examples of cyclic amides, N-acyl 2-oxindole-1-carboxamides are examples of N'-acyl amide N-carboxamides, and 2-oxindole-1-carboxamides are examples of amide N-carboxamides.

DETAILED DESCRIPTION OF THE INVENTION

The general process for the conversion of the N'-acyl amide N-carboxamide (N,N'-diacylurea) to the amide N-carboxamide (N-acylurea) is illustrated by the following reaction, wherein $R^2$ is defined as below, $R^3$ is an organic radical, and $R^4$ is an organic radical or hydrogen, such that the $R^2C(O)$— acyl group is more electron withdrawing than the $R^3C(O)$— acyl group:

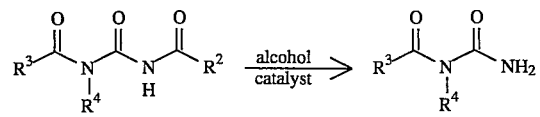

The alcoholysis reaction removes the N'-acyl group, $R^2C(O)$—, as the corresponding ester.

When the N'-acyl amide N-carboxamide is prepared from an amide and an acyl isocyanate, the amide is $R^3C(O)NHR^4$, and the acyl isocyanate is $R^2C(O)NCO$. To prepare an amide N-carboxamide corresponding to a primary amide ($R^4$=H), the N'-acyl amide N-carboxamide may alternatively be prepared by reaction of $R^3C(O)NCO$ with $R^2C(O)NH_2$.

The 2-oxindole, the N-acyl 2-oxindole-1-carboxamide, and the 2-oxindole-1-carboxamide have the formulas (I), (II), and (III), respectively:

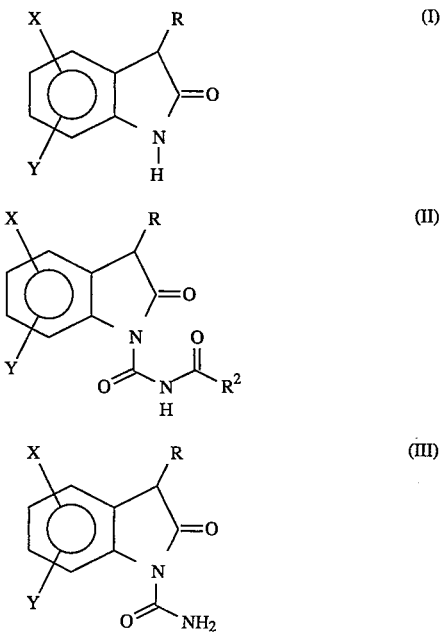

wherein
X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;
or X and Y when taken together are a 4,5-, 5,6- or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

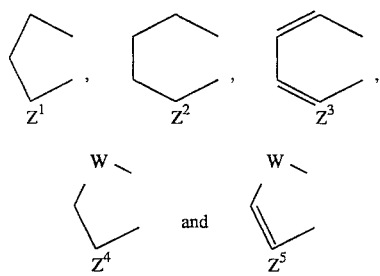

wherein W is oxygen or sulfur;
R is hydrogen or

wherein
R¹ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl, naphthyl, bicyclo[2.2.1]heptan-2-yl, bicyclo[2.2.1]hept-5-en-2-yl and —(CH2)n—Q—R⁰;
wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and trifluoromethyl; n is zero, 1 or 2; Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]-thiophene; and R⁰ is hydrogen or alkyl having 1 to 3 carbons.
R² is selected from the group consisting of substituted alkyl having 1 to 6 carbons, substituted cycloalkyl having 5 to 7 carbons, substituted phenyl, and (substituted phenyl)alkyl having 1 to 3 carbons in said alkyl,
wherein the substituents on said substituted alkyl, said substituted cycloalkyl, said substituted phenyl, and said (substituted phenyl)alkyl are electron-withdrawing and are positioned suitably so that R² is electron-withdrawing towards the carbonyl carbon to which it is bound, relative to methyl. Preferred electron-withdrawing substituents are selected from the group consisting of fluoro, chloro, and trifluoromethyl.

Particularly preferred R² are substituted alkyl having 1 to 3 carbons wherein the substituents are selected from the group consisting of fluoro and chloro. Most preferred R² are selected from the group consisting of chloromethyl, dichloromethyl, trichloromethyl, fluoromethyl, difluoromethyl, and trifluoromethyl, corresponding to N-acyl moieties (R²C(O)—) selected from the group consisting of chloroacetyl dichloracetyl, trichloroacetyl, fluoroacetyl, difluoroacetyl, and trifluoroacetyl, respectively. The acyl group comprising R², R²C(O)—, should be chosen to be more electron withdrawing than the acyl group in the 2-oxindole, or other amide, to be converted to the 2-oxindole-1-carboxamide, or other amide N-carboxamide.

The acyl isocyanate has the formula R²C(O)NCO, wherein R² is defined as above.

The aprotic weak Lewis acid catalysts useful in the process of the present invention are Lewis acids as described, for example, in *Physical Organic Chemistry*, Second Edition, by Jack Hine (McGraw-Hill Book Co., New York, 1962), in *Advanced Organic Chemistry*, Third Edition, by Jerry March (John Wiley & Sons, New York, 1985), in "Friedel-Crafts Reactions" by George Olah and David Meidar in *Kirk-Othmer Encyclopedia of Chemical Technology*, Third Edition, volume 11, pages 269–300 (John Wiley & Sons, New York, 1978), and in "Quantitative Aspects of Lewis Acidity" by D. P. N. Satchell and R. S. Satchell in *Quarterly Reviews* (The Chemical Society London), volume 25, pages 171–199. Although the formal definition of Lewis acids includes protons and protic acids (also known as Bronsted acids), as used herein, following common usage (Hine, page 44), Lewis acids includes only aprotic acids.

March, Olah and Meidar, Satchell and Satchell, and other references give guidelines on the compositional factors that determine the relative strength or weakness of Lewis acids, and order the relative Lewis acid strength (electrophilicity) among similar complexes (for example, the chlorides) of the elements. The strength of a Lewis acid is determined by the electrophilicity of its electron-accepting element as modified by ligands, radicals, or other substituents bound to it. Substituents that repel electrons decrease the electrophilicity of the electron-accepting element. For example, alkoxides as substituents typically provide weaker Lewis acids than do alkyls, which in turn provide weaker Lewis acids than do chlorides.

Strong Lewis acids (such as aluminum chloride, boron trifluoride, ferric chloride, and the like) do not appear to be effective as catalysts in the present invention, giving either poor activity or poor selectivity in the alcoholysis of the N-acyl 2-oxindole-1-carboxamides. While not wishing to be bound by theory, it appears that strong Lewis acids either irreversibly form stoichiometric complexes with the reactant, product, by-products, or alcohol, thereby giving low activity, or are so electrophilic as to give indiscriminate alcoholysis among the four amide bonds in the N-acyl 2-oxindole-1-carboxamides and those remaining in the desired product, thereby giving low selectivity. In the present invention, weak Lewis acids provide effective catalysts, giving practical reaction rates at catalytic loadings and good selectivity to the desired product. Lewis acids that are active as catalysts, reacting at least 10 moles of N-acyl 2-oxindole-1-carboxamide per mole of catalyst, and also afford good selectivity, at least 50% of theoretical production of 2-oxindole-1-carboxamide from N-trichloroacetyl 2-oxindole-1-carboxamide, are sufficiently weak Lewis adds for use in the present invention. This can be readily determined by routine experimentation such as that described in the working Examples herein.

Examples of Lewis acids useful in the present invention are compounds and complexes having the general formula $[MX_xY_yZ_z]^{n+}$ and having a vacant orbital or being able to form a vacant orbital by expanding its valence shed or by dissociating a donor ligand, wherein M is an element selected from the group boron, main group metals, transition metals, alkali metals, alkaline earth metals and rare earth metals, in a normal valence state greater than zero;

X, Y, and Z are neutral or anionic donor ligands or non-metallic atoms or radicals;

x, y, and z are each zero or an interger; and n is zero or a positive interger.

Dissociating a donor ligand includes dissociating one donor unit of a multidentate donor ligand.

Typical M include boron, aluminum, gallium, tin, thallium, lead, bismuth, titanium, zirconium, manganese, iron, cobalt, nickel, palladium, platinum, copper, zinc, mercury, lithium, magnesium, calcium, samarium, and cerium. Preferred M are tin, titanium, iron, zinc, and magnesium.

Typical X, Y, and Z are selected from halides, oxygen, oxygen-donor ligands, organic radicals and organic anions. Oxygen-donor ligands include, for example, oxygen, alkoxides, phenoxides, carboxylates, β-diketonates, sulfate, sulfonate, phosphate, phosphonate, and the like. Organic radicals include, for example, alkyl, substituted alkyl, cycloalkyl, substituted cycloalkyl, phenyl, substituted phenyl, phenylalkyl, and (substituted phenyl)alkyl radicals. Organic anions include cyclopentadienyl and substituted cyclopentadienyl anions. Preferred Lewis acids include at least one oxygen donor ligand. Most preferred include at least one alkoxide. The alkoxide may be present in the Lewis acid provided to the process or may be formed by interaction of the provided Lewis acid with the solvent. While not wishing to be bound by theory, it appears that Lewis acids containing an alkoxide ligand provide the most effective catalysts by not only coordinating the acyl carbonyl oxygen of the N-acyl 2-oxindole-1-carboxamide to render the carbonyl carbon susceptible to nucleophilic attack, but also by delivering the alkoxide nucleophile to the acyl carbonyl carbon.

Preferred weak Lewis acids are complexes of tin, titanium, iron, zinc, and magnesium containing at least one oxygen or oxygen donor ligand. Most preferred contain at least one alkoxide ligand. Some specific examples of weak Lewis acids useful in the present invention are dialkyltin(IV)dimethoxide, dicyclopentadienyltitanium(IV)dimethoxide, iron(III) tris(acetylacetonate), zinc(II) diacetate, and magnesium(II) dimethoxide. The best results in practice are obtained with dialkyltin(IV)dialkoxide or magnesium(II) dialkoxide.

Alcohols suitable for use in the present invention may be, for example, mono- or polyhydric alcohols containing primary, secondary, or tertiary hydroxyl groups as well as phenols. Mixtures of these alcohols may be used. The alcohols may be aliphatic or aromatic and may bear substituents in addition to hydroxyl groups but the substituents should preferably be non-reactive under the reaction conditions. Preferred alcohols in the present invention are lower alkanols, for example, $C_1$ to $C_4$ alkanols. Most preferred are methanol and ethanol.

The reaction of the N-acyl 2-oxindole-1-carboxamide with the alcohol may be conducted with the alcohol as the solvent or with an additional solvent that is reaction-inert. By reaction-inert solvent is meant a solvent system which does not react with the reactants or products of the reaction, or react unfavorably with the Lewis acid catalyst. The term solvent system is used to indicate that a single solvent or a mixture of two or more solvents can be used. Representative solvents are aromatic hydrocarbons such as benzene, toluene, xylene, nitrobenzene, chlorobenzene, aliphatic hydrocarbons such as pentane, hexane; dialkyl ethers such as diethyl ether, diisopropyl ether; chlorinated hydrocarbons such as methylene chloride, dichloroethylene, carbon tetrachloride, chloroform; acetonitrile, and cyclic ethers such as tetrahydrofuran, dioxane, and mixtures thereof. The solvent system used need not bring about complete solution of the reactants.

The alcoholysis is conducted at a temperature of from about 20° C. to 100° C. and preferably at from about 45° C. to 65° C. The desired 2-oxindole-1-carboxamide is recovered by known methods.

The ratio of the Lewis acid catalyst to the N-acyl 2-oxindole-1-carboxamide to be alcoholyzed is not critical, but should be a catalytic ratio less than about 1:10. In practice, ratios of 1:100 or less are effective when using the most preferred Lewis acid catalysts with N-acyl 2-oxindole-1-carboxamides comprising the most preferred N-acyl groups (—C(O)R$^2$). The minimum amount of Lewis acid relative to the N-acyl 2-oxindole-1-carboxamide depends on the activity of the specific Lewis acid, the specific N-acyl group to be alcoholyzed, the reaction temperature, and the maximum time allowed for completion of the reaction, and can be readily determined by routine experimentation.

N-acyl 2-oxindole-1-carboxamides may be obtained by the reaction of 2-oxindoles with acyl isocyanates. For example, U.S. Pat. Nos. 4,952,703 and 5,086,186 describe the production of N-trichloroacetyl-2-oxindole-1-carboxamides by the reaction of 2-oxindoles with trichloroacetyl isocyanate. Other N-acyl 2-oxindole-1-carboxamides useful in the present invention can be similarly prepared using other acyl isocyanates. Acyl isocyanates may be prepared by methods known in the art, including the reaction of acyl halides with cyanate anion and the reaction of un-N-substituted amides with oxalyl chloride.

In certain processes of the present invention, the 2-oxindole-1-carboxamide is produced from a 2-oxindole by reacting the 2-oxindole with an acyl isocyanate to produce the N-acyl 2-oxindole-1-carboxamide as an intermediate, which is then alcoholyzed to the 2-oxindole-1-carboxamide with the Lewis acid catalyst. The N-acyl 2-oxindole-1-carboxamide intermediate in this two-step process may be converted to the 2-oxindole-1-carboxamide without isolation.

The first step of this two-step process comprises reacting the 2-oxindole of formula (I), wherein X, Y and R are as defined above, in a reaction-inert solvent with the acyl isocyanate of the formula R$^2$C(O)NCO, wherein R$^2$ is as defined above, at a temperature of from about −20° C. to 150° C. In general, temperatures of from about 20° C. to 110° C. are favored. Higher or lower temperatures can be useful if desired. However, temperatures outside the favored temperature range are generally avoided for practical reasons.

The 2-oxindole and acyl isocyanate are generally reacted in molar proportions ranging from equimolar to 50% excess of acyl isocyanate (i.e., 1:1 to 1:1.5). Larger excesses of acyl isocyanate appear to afford no advantages and are not used for reasons of economy.

The thus-produced N-acyl intermediates of formula (II) can be isolated, if desired, or can be reacted directly with the alcohol, without isolation, in the same reaction vessel or another, to the 2-oxindole-1-carboxamide product of formula (III). Isolation of the N-acyl intermediate, if desired, is achieved by procedures known to those skilled in the art (e.g., filtration, evaporation of solvent or extraction).

The acyl isocyanate reactant can be used in premade form or it can be prepared in situ or ex situ as it is needed. When prepared in situ or ex situ, it can be reacted directly with the 2-oxindole without isolation. One method of preparing an acyl isocyanate for reaction without isolation comprises reacting certain acyl halides of formula $R^2C(O)X$, wherein $R^2$ is, for example, trichloromethyl or trifluoromethyl and X is fluoride, chloride, or bromide, with a cyanate salt of the formula MOCN, wherein M is an alkali metal cation (for example, lithium, sodium, potassium, or cesium), a tetralkylammonium cation, a tetraalkylphosphonium cation, or the like, m a reaction-inert solvent in a molar ratio of from about 1:1 to 1:5. Preferred combinations of cyanate salt and reaction-inert solvent provide some solubility for the cyanate salt to facilitate the reaction, although the solvent need not bring about complete solution of the cyanate salt before reaction.

Another method of preparing an acyl isocyanate for reaction with or without isolation comprises reacting an amide of formula $R^2C(O)NH_2$, wherein $R^2$ is as defined above, with oxalyl chloride in a reaction-inert solvent in a mole ratio of from about 1:1 to 1.5.

For processes in which the acyl isocyanate is prepared as needed and reacted with the 2-oxindole without isolation, and the resulting N-acyl 2-oxindole-1-carboxamide intermediate is alcoholyzed to the 2-oxindole-1-carboxamide without isolation from the solvent used to prepare the acyl isocyanate, the solvent used to prepare the acyl isocyanate should be selected to be compatible with the conditions of the Lewis acid catalyzed alcoholysis reation. This means that the solvent is reaction-inert in the Lewis acid catalyzed alcoholysis teation and that it does not undesirably inhibit the activity Lewis acid catalyst. For example, acetone and other carbonyl-containing solvents are not suitable solvents in such processes as they undergo various self-condensation and cross condensation reactions in the presence of acidic reagents.

For processes in which the acyl isocyanate is prepared by reaction of an acyl halide with an alkali cyanate salt and reacted with the 2-oxindole without isolation, and the resulting N-acyl 2-oxindole-1-carboxamide intermediate is acoholyzed to the 2-oxindole-1-carboxamide without isolation, acetonitrile has been found to be a preferred solvent. Acetonitrile provides solubility for the cyanate salt to facilitate its reaction with the acyl halide and is inert to the conditions of the Lewis acid catalyzed alcoholysis. Some weak Lewis acid catalysts useful in the present invention are not affected by the presence of acetonitrile in the alcoholysis step, for example magnesium dimethoxide. When using other Lewis acid catalysts that are inhibited by acetonitrile, for example dibutyltin(IV) dimethoxide, the acetonitrile can be readily removed from the N-acyl 2-oxindole-1-carboxamide intermediate solution by distillation before the addition of the alcohol and Lewis acid catalyst. In either case, the ready removal of acetonitrile before the alcholysis step provides for its convenient recovery for recycle.

In one practical embodiment, to sodium cyanate mixed with acetonitrile and toluene, is added trichloroacetyl chloride and the mixture is heated to complete the formation of the trichloroacetyl isocyanate. This mixture is combined with a mixture of the 2-oxindole in toluene and the resulting mixture is heated at about 90° C. until the formation of the N-trichloroacetyl 2-oxindole-1-carboxamide is substantially complete. The acetonitrile may be distilled out of the mixture at this point. Methanol and magnesium(II) dimethoxide catalyst are added and the mixture is heated at the reflux until the formation of the 2-oxindole-1-carboxamide is substantially complete. The 2-oxindole-1-carboxamide product can be recovered by known procedures.

EXAMPLES

Without further elaboration, it is believed that one skilled in the art can, using the preceding description, utilize the present invention to its fullest extent. The following specific examples are, therefore, intended to be merely illustrative, and not limitative of the disclosure in any way whatsoever.

Examples 1–6

Preparation of 5-chloro-2-oxindole-1-carboxamide by methanolysis of N-trichloroacetyl 5-chloro-2-oxindole-1-carboxamide using various weak Lewis acid catalysts In each of these examples, 3.56 grams (9.4 mmol) 94% N-trichloroacetyl 5-chloro-2-oxindole-1-carboxamide (prepared generally as described in U.S. Pat. Nos. 4,952,703 and 5,086,186) and 0.2 mmol catalyst were mixed in 25 ml 3:2 toluene:methanol and the mixture was heated at reflux until the reaction was complete as judged by thin-layer chromatography ($SiO_2$, dichloromethane, 5-chloro-2-oxindole-1-carboxamide $R_f$=0.25, N-trichloroacetyl 5-chloro-2-oxindole-1-carboxamide $R_f$=0.7). The reaction mixture was cooled to room temperature for one hour and the product was recovered by filtration, then dried in vacuo. In each example, the resulting 5-chloro-2-oxindole-1-carboxamide product was ≧99% pure by HPLC assay vs. highly purified reference standard. Table 1 lists the specific catalyst loadings, the reaction times, and the yields of these examples.

These examples show that a variety of weak Lewis acid catalysts are effective in the process of the present invention.

TABLE 1

| | Catalyst | | Reaction | Yield | |
|---|---|---|---|---|---|
| Example | identity* | amount (mg) | time (min) | (g) | (%) |
| 1 | $Mg(OEt)_2$ | 22.5 | 60 | 1.71 | 86 |
| 2 | $Mg(O_3SCF_3)_2$** | 64.5 | 60 | 1.76 | 89 |
| 3 | $Fe(acac)_3$ | 71 | 100 | 1.50 | 76 |
| 4 | $Zn(OAc)_2$ | 57 | 15 | 1.72 | 87 |
| 5 | $Cp_2Ti(OMe)_2$*** | 48 | 140 | 1.71 | 86 |
| 6 | $Bu_2Sn(OMe)_2$ | 59 | 10 | 1.86 | 94 |

*Abbreviations: Et = ethyl, Me = methyl, Bu = n-butyl, acac = acetylacetonate, Ac = acetyl, Cp = cyclopentadientyl
**Prepared from $Mg(OEt)_2$ and two equivalents $CF_3SO_3H$ in methanol.
***Prepared from $Cp_2TiCl_2$ and two equivalents NaOMe in methanol.

Example 7

Preparation of 5-chloro-2-oxindole-1-carboxamide by ethanolysis of N-trichloroacetyl 5-chloro-2-oxindole-1-carboxamide using magnesium(II) diethoxide catalyst The procedure was the same as in Example 1 except that absolute ethanol was used instead of methanol on an equal volume basis. The reaction required 30 minutes for completion and yielded 1.91 grams 5-chloro-2-oxindole-1-carboxamide in 96% yield.

Examples 1 and 7 show that various alcohols (methanol and ethanol, respectively) are useful in the process of the present invention. In Example 1, the magnesium(II) diethoxide precatalyst provided would have rapidly exchanged with the methanol solvent to provide magnesium(II) dimethoxide as the actual catalyst.

Example 8

Preparation of 5-chloro-2-oxindole-1-carboxamide from 5-chloro-2-oxindole via methanolysis of N-trichloroacetyl 5-chloro-2-oxindole-1-carboxamide using magnesium(II) dimethoxide catalyst A slurry of 2.16 grams (33.75 mmol) sodium cyanate in 7 ml acetonitrile and 8 ml toluene was treated with 6.14 grams (33.75 mmol) trichloroacetylchloride and heated to 65°–70° C. for 1.5 hours, then cooled to room temperature. This mixture (a solution of trichloroacetyl isocyanate with slurried sodium chloride) was added to a slurry of 4.19 gram (25.0 mmol) 5-chloro-2-oxindole in 20 ml toluene at 90° C., which had first been heated to reflux to remove any water. After an additional 15 minutes at 90° C., the formation of N-trichloroacetyl 5-chloro-2-oxindole-1-carboxamide was complete as judged by thin-layer chromatography. 13 ml of acetonitrile and toluene were then distilled from the mixture under vacuum, 200 mmHg. 10 ml methanol and 56 mg (0.5 mmol) magnesium(II) diethoxide were added to the remaining mixture. The resulting mixture was heated to reflux for 70 minutes after which the methanolysis reaction was complete as judged by thin-layer chromatography. The mixture was cooled in an ice bath for 30 minutes and filtered. The filtered solid was washed with toluene, then dried in vacuo at 50° C. for one hour. The solid was then slurried with water to dissolve sodium chloride. The product was recovered by filtration and dried vacuo (1 mmHg) at 60° C. for three hours. Yield 4.82 grams tan solid, 5-chloro-2-oxindole-1-carboxamide ($^1$H-NMR); 92% yield on 5-chloro-2-oxindole. Purity 98.9% (HPLC).

The example shows the effectiveness of the two-step process from a 2-oxindole with ex situ formation of the acyl isocyanate as needed. When the 2-oxindole is dry, or the yield loss due to water is acceptable, this process is easily converted to a single vessel process with in situ formation of the acyl isocyanate by adding the 5-chloro-2-oxindole and additional toluene to the acyl isocyanate solution in the vessel in which it was prepared.

Example 9

Preparation of 5-chloro-2-oxindole-1-carboxamide from 5-chloro-2-oxindole via ethanolysis of N-trichloroacetyl 5-chloro-2-oxindole-1-carboxamide using magnesium(II) diethoxide catalyst The procedure was the same as in Example 8 except that absolute ethanol was used instead of methanol on an equal volume basis. The ethanolysis reaction occurred over 30 minutes at reflux. The final reaction mixture was cooled one hour at room temperature, then in an ice bath for 30 minutes. The product was then recovered as in Example 8. Yield 4.80 grams 5-chloro-2-oxindole-1-carboxamide; 91% yield on 5-chloro-2-oxindole.

Examples 8 and 9 show the that various alcohols (methanol and ethanol, respectively) are useful in the two-step process of the present invention.

Example 10

Preparation of 2-oxindole-1-carboxamide from 2-oxindole via methanolysis of N-trichloroacetyl 2-oxindole-1-carboxamide using magnesium(II) dimethoxide catalyst The procedure was the same as in Example 8 except that 3.33 grams (25 mmol) 2-oxindole was reacted instead of 5-chloro-2-oxindole. The methanolysis reaction occurred over 90 minutes at reflux. After the final reaction mixture was cooled in an ice bath for 30 minutes, 10 ml of hexane was added and it was cooled in an ice bath for an additional 30 minutes before filtration. The product was then recovered as in Example 8. Yield 3.75 grams (85% on 2-oxindole) 2-oxindole-1-carboxamide ($^1$H-NMR, m.p. 179°–180° C.).

Examples 8 and 10 show the general effectiveness of the present invention for the preparation of the 1-carboxamides of various 2-oxindoles. The present invention is also effective for the preparation of other 2-oxindole-1-carboxamides demonstrated in the working Examples of U.S. Pat. Nos. 4,952,703 and 5,086,186.

Example 11

Preparation of 5-chloro-2-oxindole-1-carboxamide from 5-chloro-2-oxindole via methanolysis of N-trichloroacetyl 5-chloro-2-oxindole-1-carboxamide using zinc diacetate catalyst The procedure was the same as in Example 8 except that 50 mg (0.27 mmol) zinc(II) diacetate was added as catalyst for the methanolysis reaction instead of magnesium(II) dimethoxide. After 90 minutes at reflux, the methanolysis reaction was judged by thin-layer chromatography to be relatively slow. An additional 50 mg zinc(II) diacetate was added and the reaction was complete after 10 additional minutes at the reflux. The product was recovered as in Example 8. Yield 4.38 grams 5-chloro-2-oxindole-1-carboxamide; 83% yield on 5-chloro-2-oxindole.

The inventor speculates that the first added zinc acetate was inhibited by residual acetonitrile in the solution of the N-trichloroacetyl 5-chloro-2-oxindole-1-carboxamide, but that the second addition of zinc acetate provided active catalyst in excess of the residual acetonitrile. Compare the rapid reaction rate using zinc acetate relative to magnesium alkoxide in the reactions of Examples 4 and 1, respectively, in the absence of acetonitrile.

Example 12

Preparation of 5-chloro-2-oxindole-1-carboxamide from 5-chloro-2-oxindole via methanolysis of N-trichloroacetyl 5-chloro-2-oxindole-1-carboximide using di(n-butyl)tin(IV) dimethoxide catalyst The procedure was the same as in Example 8 except for the following changes: 10 ml of acetonitrile and toluene were then distilled from the N-trichloroacetyl 5-chloro-2-oxindole-1-carboxamide mixture before adding 10 ml methanol and 50 mg (0.17 mmol) di(n-butyl)tin(IV) dimethoxide as catalyst (instead of magnesium(II) dimethoxide) for the methanolysis reaction. The resulting mixture was heated to reflux for 2 hours, then cooled in an ice bath for about 1 hour. The product was recovered as in Example 8. Yield 4.28 grams 5-chloro-2-oxindole-1-carboxamide; 82% yield on 5-chloro-2-oxindole.

Examples 8, 11, and 12 show the utility of weak Lewis adds comprised of different elements in the two step process with ex situ formation of the acyl isocyanate.

Example 13

Preparation of 5-chloro-2-oxindole-1-carboxamide from 5-chloro-2-oxindole via methanolysis of N-trichloroacetyl 5-chloro-2-oxindole-1-carboxamide using di(n-butyl)tin(IV)oxide precatalyst The procedure was the same as in Example 12 except that 50 mg (0.20 mmol) di(n-butyl)tin(IV) oxide was used as precatalyst and the 10 ml methanol contained 5 drops acetic acid. Yield 4.50 grams 5-chloro-2-oxindole-1-carboxamide; 86% yield on 5-chloro-2-oxindole.

When di(n-butyl)tin(IV) oxide, an oligomeric solid, is used as precatalyst with high purity reactants, there is an induction period which can be eliminated by adding small amounts of a weak protic add, in this case acetic add. The weak protic add is believed to catalyze the conversion of the di(n-butyl)tin(IV)oxide into di(n-butyl)tin(IV) dialkoxide in the alcoholic solution. The small amount of weak protic acid used in this example is insufficient by itself to catalyze the desired alcoholysis reaction at any reasonable rate.

Example 14

Preparation of 5-chloro-2-oxindole-1-carboxamide from 5-chloro-2-oxindole via methanolysis of N-chloroacetyl 5-chloro-2-oxindole-1-carboxamide using di(n-butyl)tin(IV) dimethoxide catalyst To A slurry of 2.34 grams (25 mmol) chloroacetamide in 25 ml toluene was added 3.18 grams (25 mmol) oxalyl chloride and the mixture was heated to 60°–80° C., resulting in gas evolution. After 30 minutes at this temperature, the resulting mixture was heated to reflux for 1 hour, during which 5 ml toluene was removed by distillation, then cooled to room temperature. This mixture, containing chloroacetyl isocyanate, was added to a slurry of 3.35 gram (20.0 mmol) 5-chloro-2-oxindole in 10 ml toluene that was at the reflux temperature. After an additional 30 minutes at reflux, the formation of N-chloroacetyl 5-chloro-2-oxindole-1-carboxamide was near complete thin-layer chromatagraphy. Some residual 5-chloro-2-oxindole was noted. To this cooled slurry was added 50 mg (0.20 mmol) di(n-butyl)tin(IV) oxide as precatalyst and 10 ml methanol contained 5 drops acetic acid. The mixture was heated to reflux for two hours, resulting in a slow reaction as judged by thin-layer chromatagraphy. To accelerate the reaction, additional catalyst, 60 mg (0.20 mmol) di(n-butyl)tin(IV) dimethoxide was then added and the mixture was kept at the reflux overnight. Thin-layer chromatagraphy then showed only the desired 5-chloro-2-oxindole-1-carboxamide and residual 5-chloro-2-oxindole. The mixture was cooled to room temperature and filtered. The filtered solid was dried in vacuo. Yield 3.76 grams light tan solid, 5-chloro-2-oxindole-1-carboxamide; 89% yield on 5-chloro-2-oxindole.

This example shows another N'-acyl group ($R^2C(O)$—), in this case, monochloroacetyl, useful in the process of the present invention.

Example 15

Preparation of 5-chloro-2-oxindole-1-carboxamide from 5-chloro-2-oxindole via methanolysis of N-trichloroacetyl 5-chloro-2-oxindole-1-carboxamide using di(n-butyl)tin(IV) dimethoxide catalyst A slurry of 0.88 grams (13.5 mmol) sodium cyanate in 6 ml acetonitrile and 6 ml toluene was treated with 2.46 grams (13.5 mmol) trichloroacetylchloride and heated to 45°–50° C. for 1.5 hours, then cooled to room temperature and diluted with 8 ml additional toluene. This mixture was added over 5 minutes to a slurry of 1.68 gram (10.0 mmol) 5-chloro-2-oxindole in 12 ml toluene at 85°–90° C., which had first been heated to reflux to remove a small amount of water. After an additional 30 minutes at reflux, the formation of N-trichloroacetyl 5-chloro-2-oxindole-1-carboxamide was complete as judged by thin-layer chromatography. 12 ml of acetonitrile and toluene were then distilled from the mixture under vacuum, 200 mmHg. After the remaining mixture was cooled to room temperature, a solution of 55 mg (0.186 mmol) di(n-butyl)tin(IV) dimethoxide in 10 ml methanol was added. The resulting mixture was heated to reflux for 70 minutes. The mixture was cooled in an ice bath for 3 hours and filtered. The filtered solid was dried in vacuo, then slurried with water containing a small proportion of acetone to dissolve sodium chloride. The product was recovered by filtration and dried in vacuo. Yield 1.84 grams 5-chloro-2-oxindole-1-carboxamide; 88% yield on 5-chloro-2-oxindole. Purity 98.4% (HPLC).

Example 16

Preparation of 5-chloro-2-oxindole-1-carboxamide from 5-chloro-2-oxindole via methanolysis of N-trichloroacetyl 5-chloro-2-oxindole-1-carboxamide using dibutyltin(IV)oxide precatalyst The procedure was the same as in Example 15 except that 50 mg (0.20 mmol) di(n-butyl)tin(IV) oxide was added with the 10 ml methanol, which also contained 4 drops of acetic acid. The resulting mixture was heated to reflux for 30 minutes then cooled in an ice bath. The product was recovered as in Example 15. Yield 1.84 grams 5-chloro-2-oxindole-1-carboxamide; 88% yield on 5-chloro-2-oxindole.

Example 17

Preparation of 5-chloro-2-oxindole-1-carboxamide from 5-chloro-2-oxindole via methanolysis of N-trichloroacetyl 5-chloro-2-oxindole-1-carboxamide using bis(chlorodibutyltin)oxide precatalyst The procedure was the same as in Example 15 except that 50 mg (0.181 mg-atom tin) bis(chlorodibutyltin)oxide was added with the 10 ml methanol, which also contained 4 drops of acetic acid. The resulting mixture was heated to reflux for 40 minutes to complete the methanolysis reaction. The product was recovered as in Example 15. Yield 1.78 grams 5-chloro-2-oxindole-1-carboxamide; 85% yield on 5-chloro-2-oxindole.

Example 18 (Comparative)

Attempted preparation of 5-chloro-2-oxindole-1-carboxamide from 5-chloro-2-oxindole via methanolysis of N-chloroacetyl 5-chloro-2-oxindole-1-carboxamide using sulfuric acid catalyst and the one-pot adaptation prescribed in U.S. Pat. Nos. 4,952,703 and 5,086,186

The prescription of these patents for a one-pot process is quoted under Background Of The Invention, above. A slurry of 1.05 grams (13 mmol) potassium cyanate in 15 ml acetone at room temperature was treated with 1.82 grams (10 mmol) trichloroacetylchloride, resulting in a exothermic temperature rise. The mixture was cooled to room temperature and held at room temperature for 1.5 hours. To this mixture was added 1.68 grams (10 mmol) 5-chloro-2-oxindole and the resulting mixture was heated to reflux for 1.5 hours. To this mixture at the reflux was added 10 ml methanol containing 3 drops of concentrated sulfuric add, and the resulting mixture was kept at the reflux. Thin layer chromatography showed only a slow reaction. After 2 hours at reflux, an additional 4 drops of concentrated sulfuric acid were added. After an additional 1.5 hours at reflux, the mixture was cooled to room temperature and filtered. The filtered solid was dried, then slurried with water to dissolve sodium chloride. The product was recovered by filtration and dried in vacuo. Yield 0.55 grams 5-chloro-2-oxindole-1-carboxamide; 26% yield on 5-chloro-2-oxindole.

This example shows that the one-pot adaptation prescribed in U.S. Pat. Nos. 4,952,703 and 5,086,186 is ineffective for practical use. Compare Examples 15–17 showing the effectiveness of processes of the present invention, at the same scale of operation.

Example 19

Preparation of 5-chloro-2-oxindole-1-carboxamide from 5-chloro-2-oxindole via methanolysis of N-trichloroacetyl 5-chloro-2-oxindole-1-carboxamide using di(n-butyl)tin(IV)oxide precatalyst To a 500 ml three neck flask equipped with a reflux condenser, thermometer, 250 ml addition funnel, magnetic stirrer, and water bath was charged 43.9 grams (0.675 mole) sodium cyanate, 75 ml acetonitrile, and 125 ml toluene. To the addition funnel was added 123 grams (0.675 mole) trichloroacetyl chloride. The trichloroacetyl chloride was added under nitrogen atmosphere at a rate to maintain the reaction temperature between 30°–40° C. After the addition was complete (30 min) the water bath was replaced with an electric heating mantle and the mixture was maintained at 65°–70° C. for 1.5 hour and then cooled to room temperature with the water bath, giving a solution of trichloroacetyl isocyanate containing slurried sodium chloride.

To a three neck 1 L flask equipped with mechanical stirrer, thermometer, heating mantle, and solvent distillation head was charged 83.75 g (0.500 mole) 5-chloro-2-oxindole (98.9% pure by HPLC) and 450 ml toluene. This slurry was heated under a nitrogen atmosphere and 50 ml of toluene containing some water was distilled out. The thermometer was replaced with a 500 ml addition funnel containing the trichloroacetyl isocyanate/sodium chloride slurry. The thermometer on the distillation head was lowered into the 5-chloro-2-oxindole mixture, whose temperature was allowed to fall to 90° C. At that temperature, the addition of the trichloroacetyl isocyanate mixture was started. During the addition (30 min), the reaction temperature was maintained between 80°–90° C. with heating. After an additional 30 min at 90° C., the addition funnel was replaced with the thermometer and the apparatus was adapted for distillation. Vacuum (200 mmHg) was slowly applied and 200 ml of acetonitrile/toluene was distilled out.

The reaction mixture was then placed under a nitrogen atmosphere and 0.9 grams (3.6 mmole) di-n-butyltin oxide and 200 ml methanol containing 2.0 grams acetic add were added. This mixture was heated at reflux for 5 hours, then cooled to room temperature, left overnight, then further cooled to 5° C. with an ice bath and held at this temperature for 1.5 hours. The resulting slurry was filtered and the filtered solids were washed with 500 ml toluene that was prechilled to 10° C. The recovered solids were dried in vacuo (2 hr, 50° C., 1 mmHg), then slurried in 850 ml water to dissolve the sodium chloride. To help wet the solids, 75 ml acetone was added. The remaining slurried solid was filtered, washed with 150 ml water and dried in vacuo (5 hr, 60° C., 1 mmHg). Yield 86.8 grams tan-brown free-flowing powder, 5-chloro-2-oxindole-1-carboxamide ($^1$H-NMR); 82.5% yield on 5-chloro-2-oxindole (adjusted for purifies of starting material and product). Purity 98.9% (HPLC).

This example shows the process of the present invention on a larger scale than the preceding examples, using procedures all readily adapted and scaled to large scale production. Di(n-butyl)tin dimethoxide can be substituted for di(n-butyl)tin oxide in this example, in which case no acetic acid need be included.

Example 20

Preparation of 5-chloro-2-oxindole-1-carboxamide from 5-chloro-2-oxindole via methanolysis of N-trichloroacetyl 5-chloro-2-oxindole-1-carboxamide using magnesium(II)dimethoxide catalyst The procedure was the same as for Example 19 through the methanolysis reaction with the exceptions that 170 ml of acetonitrile/toluene was removed in the distillation step before the methanolysis reaction, that 6.0 ml of 10% magnesium dimethoxide in methanol, corresponding to 0.49 grams (5.7 mmol) magnesium(II) dimethoxide, was added as the catalyst for the methanolysis reaction (instead of di(n-butyl)tin oxide) and the acetic acid was omitted, and that the methanolysis reaction was conducted at the reflux temperature for 1.75 hours. Then, the final methanolysis reaction was cooled to 15°–20° C. for 2 hours. The resulting slurry was filtered and the filtered solids were washed with 400 ml toluene. The recovered solids were dried in vacuo (4 hr, 50° C., 1 mmHg), then slurried in 800 ml water to dissolve the sodium chloride. To help wet the solids, 50 ml acetone was added. The remaining slurried solid was filtered, washed with 200 ml water and dried in vacuo (10 hr, 60° C., 1 mmHg). Yield 92.3 grams tan-brown flee-flowing powder, 5-chloro-2-oxindole-1-carboxamide ($^1$H-NMR); 86.9% yield on 5-chloro-2-oxindole (corrected for purities of the starting material and product). Purity 98.1% (HPLC).

This shows another example of the process of the present invention, using another weak Lewis acid catalyst, on the scale of Example 19, using procedures readily adapted and scaled to large scale production.

Example 21 (Comparative)

Attempted preparation of 5-chloro-2-oxindole-1-carboxamide from 5-chloro-2-oxindole via methanolysis of N-chloroacetyl 5-chloro-2-oxindole-1-carboxamide using a protic acid catalyst The procedure was the same as for Example 19 through the methanolysis reaction with the exceptions that the 5-chloro-2-oxindole was 94.2% pure, that 5.0 grams 85% phosphoric acid was added as the catalyst for the methanolysis reaction (instead of di(n-butyl)tin oxide) and the acetic acid was omitted, and that the methanolysis reaction was conducted at the reflux temperature for 2.5 hours (after which the methanolysis was complete as judged by TLC). Then, the final methanolysis reaction was cooled with an ice bath for 3 hours. The resulting slurry was filtered and the filtered solids were washed with toluene. The recovered solids were dried in vacuo (4 hr, 60° C., 1 mmHg), then slurried in 850 ml water to dissolve the sodium chloride. To help wet the solids, 25 ml acetone was added. The remaining slurried solid was filtered, washed with 150 ml water and dried in vacuo (6 hr, 60° C., 1 mmHg). Yield 88.7 grams tan free-flowing powder, impure 5-chloro-2-oxindole-1-carboxamide; 78% yield on 5-chloro-2-oxindole (corrected for purifies of the starting material and product). Purity 87.5% (HPLC).

The product contained one prominant impurity that was also present in the methanolysis reaction filtrate (TLC). This by-product was isolated by crystallization from a reaction filtrate and purified by recrystallizations. It was identified by $^1$H-NMR and mass spectrometry as having formula (V), wherein X=5-Cl, Y=H, and R=H. This by-product is not detected in the 5-chloro-2-oxindole-1-carboxamide products of Examples 19 and 20. Comparison of Examples 19 and 20 with this example shows that weak Lewis acid catalysts used in the present invention can give greater selectivity and yield in the alcoholysis reaction, and higher purity carboxamide product.

Example 22

Preparation of benzoyl urea from benzamide via methanolysis of N-benzoyl-N'-trichloroacetyl urea using magnesium (II) dimethoxide catalyst A slurry of 0.81 grams (12.5 mmol) sodium cyanate in 5 ml acetonitrile and 5 ml toluene was treated with 2.27 grams (12.5 mmol) trichloroacetylchloride and heated to 60° C. for 1 hours, then cooled to room temperature. This mixture was added to a slurry of 1.21 grams (10.0 mmol) benzamide in 20 ml toluene at 50° C. and the resulting mixture was kept at 50° C. for 30 minutes. Then, 10 ml methanol and 30 mg (0.26 mmol) magnesium(II) diethoxide were added and the mixture was heated at the reflux for 1.5 hours. The resulting mixture was treated with 10 ml hexane and cooled in an ice bath for 30 minutes. The resulting slurry was filtered and the filtered solid was slurried with water to dissolve the sodium chloride. The product was recovered by filtration and dried in vacuo. Yield 1.41 grams benzoyl urea (m.p. 212°–213° C.); 86% yield on benzamide.

The example shows the conversion of a primary amide, benzamide, to an amide N-carboxamide, benzoyl urea, via alcoholysis of a N'-acyl amide N-carboxamide, N-benzoyl-N'-trichloroacetyl urea by the process of the present invention. It also shows that the magnesium(II) dialkoxide alcoholysis catalysts tolerate the presence of a nitrile solvent in the alcoholysis reaction.

Example 23

Preparation of caprolactam N-carboxamide from caprolactam via methanolysis of N'-trichloroacetyl caprolactam N-carboxamide using magnesium (II) dimethoxide catalyst The procedure was the same as for Example 22 through the methanolysis reaction with the exception that 1.13 grams (10 mmol) caprolactam was reacted (instead of benzamide) and that the methanolysis reaction was conducted at the reflux temperature for 1 hour. The final methanolysis reaction mixture was filtered to remove the sodium chloride and the filtrate, containing the product, was reduced in volume by solvent evaporation. The product was isolated by flash chromatography (silica gel, 10% ethylacetate/methylene chloride). Yield 0.82 grams caprolactam N-carboxamide ($^1$H-NMR); 53% yield on caprolactam.

The example shows the conversion of a cyclic secondary amide, caprolactam, to an amide N-carboxamide, caprolactam N-carboxamide, via alcoholysis of a N'-acyl amide N-carboxamide, N'-trichloroacetyl caprolactam N-carboxamide by the process of the present invention.

The present inventions have been shown by both description and examples. The examples are only examples and cannot be construed to limit the scope of the invention. One of ordinary skill in the art will envision equivalents to the inventive processes described by the following claims which are within the scope and spirit of the claimed invention.

I claim as my invention:

1. A process for preparing an amide N-carboxamide, comprising:

reacting a N'-acyl amide N-carboxamide with an alcohol in the presence of an aprotic weak Lewis acid catalyst to produce said amide N-carboxamide.

2. A process for preparing an amide N-carboxamide, comprising:

reacting an amide selected from the group consisting of primary and secondary amides with an acyl isocyanate to produce a N'-acyl amide N-carboxamide; and reacting said N'-acyl amide N-carboxamide with an alcohol in the presence of an aprotic weak Lewis acid catalyst to produce said amide N-carboxamide.

3. The process of claim 1 or 2 wherein said amide is a cyclic amide.

4. The process of claim 3 wherein said cyclic amide is a 2-oxindole.

5. The process of claim 1 or 2 wherein said aprotic weak Lewis acid catalyst is selected from the group consisting of Lewis acidic compounds and complexes of tin, titanium, iron, zinc, and magnesium.

6. The process of claim 5 wherein said aprotic weak Lewis acid catalyst comprises an oxygen donor ligand.

7. The process of claim 1 or 2 wherein said aprotic weak Lewis acid catalyst is selected from the group consisting of dialkyltin(IV) dialkoxides and magnesium(II) dialkoxides.

8. The process of claim 1 or 2 wherein said N'-acyl amide N-carboxamide comprises an N'-acyl moiety selected from the group consisting of chloroacetyl, dichloroacetyl, trichloroacetyl, fluoroacetyl, difluoroacetyl, and trifluoroacetyl.

9. The process of claim 8 wherein said N-acyl moiety is trichloroacetyl.

10. The process of claim 1 or 2 wherein said alcohol is selected from the group consisting of $C_1$ to $C_4$ alkanols.

11. The process of claim 10 wherein said alcohol is selected from the group consisting of methanol and ethanol.

* * * * *